(12) United States Patent
Argento et al.

(10) Patent No.: US 9,486,311 B2
(45) Date of Patent: Nov. 8, 2016

(54) HYDROPHILIC AIOL WITH BONDING

(71) Applicant: Shifamed Holdings, LLC, Campbell, CA (US)

(72) Inventors: Claudio Argento, Felton, CA (US); Bob Vaughan, Los Gatos, CA (US); Amr Salahieh, Saratoga, CA (US); Tom Saul, Moss Beach, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 0 days.

(21) Appl. No.: 14/181,145

(22) Filed: Feb. 14, 2014

(65) Prior Publication Data

US 2014/0228949 A1 Aug. 14, 2014

Related U.S. Application Data

(60) Provisional application No. 61/764,699, filed on Feb. 14, 2013, provisional application No. 61/764,715, filed on Feb. 14, 2013.

(51) Int. Cl.
*B29C 65/00* (2006.01)
*B32B 37/00* (2006.01)
(Continued)

(52) U.S. Cl.
CPC ........... *A61F 2/1648* (2013.01); *A61F 2/1635* (2013.01); *B29D 11/00028* (2013.01);
(Continued)

(58) Field of Classification Search
CPC ... B29C 65/00; B29C 65/48; B29C 65/4805; B29C 65/483; B32B 37/0076; B32B 37/12; B29D 11/023; B29D 11/0073; B29D 11/0074; B29D 11/00942; A61F 2/16; A61F 2/1613; A61F 2/1616; A61F 2/1624; A61F 2/1635; A61F 2/1648; A61F 2/1681; A61F 2002/1681; A61F 2002/169; G02B 3/14; G02B 7/025; B24B 13/0006
USPC ........... 156/60, 83, 145, 146, 156, 242, 245, 156/153, 250, 267, 272.2, 275.5, 292, 156/307.1, 325, 326, 327, 304.1, 304.2, 156/304.5; 623/4.1, 6.11, 6.13, 6.32, 6.34, 623/6.37
See application file for complete search history.

(56) References Cited

U.S. PATENT DOCUMENTS 4,440,918 A 4/1984 Rice et al.
4,663,409 A 5/1987 Friends et al.
(Continued)

FOREIGN PATENT DOCUMENTS

AU 2006/200142 A1 7/2006
EP 0604369 A1 6/1994
(Continued)

OTHER PUBLICATIONS

International search report and written opinion dated Aug. 28, 2014 for PCT Application No. US2014/026817.
(Continued)

*Primary Examiner* — Philip Tucker
*Assistant Examiner* — Brian R Slawski
(74) *Attorney, Agent, or Firm* — Perkins Coie LLP

(57) ABSTRACT

An accommodating intraocular lens comprises a first lens component, a second lens component, and an adhesive between portions of the two lens components. The cured adhesive bonds the lens components to form a fluid chamber. The lens components are bonded to one another along a seam which extends circumferentially along at least a portion of the lens components. The lens components may comprise the same polymer material. The cured adhesive also comprises the polymer or a prepolymer of the polymer to provide increased strength. The polymer is hydratable such that the lens components and the cured adhesive therebetween can swell together to inhibit stresses between the lens components and the cured adhesive.

16 Claims, 3 Drawing Sheets

(51) Int. Cl.
  *A63B 39/00*    (2006.01)
  *A63B 41/00*    (2006.01)
  *B32B 38/10*    (2006.01)
  *B29C 47/00*    (2006.01)
  *A61F 2/16*     (2006.01)
  *B29D 11/00*    (2006.01)
  *B29D 11/02*    (2006.01)
  *B29C 65/48*    (2006.01)

(52) U.S. Cl.
  CPC ........ B29D11/026 (2013.01); *A61F 2002/169* (2015.04); *B29C 65/483* (2013.01); *B29D 11/023* (2013.01); *B32B 37/0076* (2013.01)

(56) References Cited

U.S. PATENT DOCUMENTS

| | | |
|---|---|---|
| 4,709,996 A | 12/1987 | Michelson |
| 4,842,601 A | 6/1989 | Smith |
| 4,932,966 A | 6/1990 | Christie et al. |
| 5,074,942 A * | 12/1991 | Kearns et al. ............... 156/154 |
| 5,211,662 A * | 5/1993 | Barrett et al. ............... 623/6.6 |
| 5,405,386 A | 4/1995 | Rheinish et al. |
| 5,423,929 A * | 6/1995 | Doyle et al. ............... 156/73.1 |
| 5,556,929 A | 9/1996 | Yokoyama et al. |
| 5,612,391 A | 3/1997 | Chabrecek et al. |
| 5,807,944 A | 9/1998 | Hirt et al. |
| 5,891,931 A | 4/1999 | Leboeuf et al. |
| 5,914,355 A | 6/1999 | Kunzler |
| 5,945,465 A | 8/1999 | Ozark et al. |
| 5,945,498 A | 8/1999 | Hopken et al. |
| 6,140,438 A | 10/2000 | Ojio et al. |
| 6,346,594 B1 | 2/2002 | Watanabe et al. |
| 6,447,920 B1 | 9/2002 | Chabrecek et al. |
| 6,465,056 B1 | 10/2002 | Chabrecek et al. |
| 6,521,352 B1 | 2/2003 | Chabrecek et al. |
| 6,558,420 B2 | 5/2003 | Green |
| 6,582,754 B1 | 6/2003 | Pasic et al. |
| 6,586,038 B1 | 7/2003 | Chabrecek et al. |
| 6,630,243 B2 | 10/2003 | Valint, Jr. et al. |
| 6,660,035 B1 | 12/2003 | Lang et al. |
| 6,685,741 B2 | 2/2004 | Landreville et al. |
| 6,713,583 B2 | 3/2004 | Liao et al. |
| 6,730,123 B1 | 5/2004 | Klopotek |
| 6,734,321 B2 | 5/2004 | Chabrecek et al. |
| 6,747,090 B2 | 6/2004 | De Groot et al. |
| 6,761,737 B2 | 7/2004 | Zadno-azizi et al. |
| 6,764,511 B2 | 7/2004 | Zadno-azizi et al. |
| 6,767,363 B1 | 7/2004 | Bandhauer et al. |
| 6,767,979 B1 | 7/2004 | Muir et al. |
| 6,786,934 B2 | 9/2004 | Zadno-azizi et al. |
| 6,818,017 B1 | 11/2004 | Shu |
| 6,818,158 B2 | 11/2004 | Pham et al. |
| 6,835,410 B2 | 12/2004 | Chabrecek et al. |
| 6,846,326 B2 | 1/2005 | Zadno-azizi et al. |
| 6,858,040 B2 | 2/2005 | Nguyen et al. |
| 6,884,261 B2 | 4/2005 | Zadno-azizi et al. |
| 6,893,595 B1 | 5/2005 | Muir et al. |
| 6,893,685 B2 | 5/2005 | Qiu et al. |
| 6,899,732 B2 | 5/2005 | Zadno-azizi et al. |
| 6,935,743 B2 * | 8/2005 | Shadduck ............... 351/159.04 |
| 6,969,403 B2 | 11/2005 | Peng et al. |
| 7,041,134 B2 | 5/2006 | Nguyen et al. |
| 7,087,080 B2 | 8/2006 | Zadno-azizi et al. |
| 7,118,596 B2 | 10/2006 | Zadno-azizi et al. |
| 7,198,640 B2 | 4/2007 | Nguyen |
| 7,217,778 B2 | 5/2007 | Verbruggen et al. |
| 7,226,478 B2 | 6/2007 | Ting et al. |
| 7,416,562 B2 | 8/2008 | Gross |
| 7,438,723 B2 | 10/2008 | Esch |
| 7,452,378 B2 | 11/2008 | Zadno-azizi et al. |
| 7,468,397 B2 | 12/2008 | Schorzman et al. |
| 7,479,530 B2 | 1/2009 | Hughes et al. |
| 7,557,231 B2 | 7/2009 | Schorzman et al. |
| 7,588,334 B2 | 9/2009 | Matsushita et al. |
| 7,591,849 B2 | 9/2009 | Richardson |
| 7,601,766 B2 | 10/2009 | Schorzman et al. |
| 7,637,947 B2 | 12/2009 | Smith et al. |
| 7,714,090 B2 | 5/2010 | Iwamoto et al. |
| 7,744,603 B2 | 6/2010 | Zadno-azizi et al. |
| 7,744,646 B2 | 6/2010 | Zadno-azizi et al. |
| 7,781,558 B2 | 8/2010 | Schorzman et al. |
| 7,842,087 B2 | 11/2010 | Ben Nun |
| 7,883,540 B2 | 2/2011 | Niwa et al. |
| 7,906,563 B2 | 3/2011 | Huang et al. |
| 7,942,929 B2 | 5/2011 | Linhardt et al. |
| 8,003,710 B2 | 8/2011 | Medina et al. |
| 8,025,823 B2 | 9/2011 | Pham et al. |
| 8,034,107 B2 | 10/2011 | Stenger |
| 8,048,155 B2 | 11/2011 | Shadduck |
| 8,071,703 B2 | 12/2011 | Zhou et al. |
| 8,105,623 B2 | 1/2012 | Schorzman et al. |
| 8,158,712 B2 | 4/2012 | Your |
| 8,187,325 B2 | 5/2012 | Zadno-azizi et al. |
| 8,211,955 B2 | 7/2012 | Chang et al. |
| 8,222,360 B2 | 7/2012 | Liao |
| 8,251,509 B2 | 8/2012 | Dai et al. |
| 8,283,429 B2 | 10/2012 | Zhou et al. |
| 8,328,869 B2 | 12/2012 | Smiley et al. |
| 8,357,771 B2 | 1/2013 | Medina et al. |
| 8,377,123 B2 | 2/2013 | Evans et al. |
| 8,414,646 B2 | 4/2013 | De Juan et al. |
| 8,420,711 B2 | 4/2013 | Awasthi et al. |
| 8,425,595 B2 | 4/2013 | Tsai et al. |
| 8,425,599 B2 | 4/2013 | Shadduck |
| 8,425,926 B2 | 4/2013 | Qiu et al. |
| 8,430,928 B2 | 4/2013 | Liao |
| 8,454,688 B2 | 6/2013 | Esch et al. |
| 8,486,142 B2 | 7/2013 | Bumbalough et al. |
| 8,500,806 B1 | 8/2013 | Phillips |
| 8,585,758 B2 | 11/2013 | Woods |
| 8,603,166 B2 | 12/2013 | Park |
| 8,609,745 B2 | 12/2013 | Medina et al. |
| 8,663,510 B2 | 3/2014 | Graney et al. |
| 8,680,172 B2 | 3/2014 | Liao |
| 8,728,158 B2 | 5/2014 | Whitsett |
| 8,759,414 B2 | 6/2014 | Muller-lierheim et al. |
| 8,784,485 B2 | 7/2014 | Tsai et al. |
| 8,827,447 B2 | 9/2014 | Awasthi et al. |
| 8,835,525 B2 | 9/2014 | Kuyu et al. |
| 8,851,670 B2 | 10/2014 | Dai et al. |
| 8,863,749 B2 | 10/2014 | Gooding et al. |
| 8,877,227 B2 | 11/2014 | Ravi |
| 8,899,745 B2 | 12/2014 | Domschke |
| 8,900,298 B2 | 12/2014 | Anvar et al. |
| 8,956,409 B2 | 2/2015 | Ben Nun |
| 8,968,399 B2 | 3/2015 | Ghabra |
| 8,993,651 B2 | 3/2015 | Chang et al. |
| 9,005,492 B2 | 4/2015 | Chang et al. |
| 9,005,700 B2 | 4/2015 | Bothe et al. |
| 9,006,359 B2 | 4/2015 | Zhang et al. |
| 9,011,532 B2 | 4/2015 | Bumbalough et al. |
| 9,023,915 B2 | 5/2015 | Hu et al. |
| 9,034,035 B2 | 5/2015 | Betser et al. |
| 9,039,174 B2 | 5/2015 | Awasthi et al. |
| 9,044,302 B2 | 6/2015 | Gooding et al. |
| 9,052,439 B2 | 6/2015 | Samuel et al. |
| 9,052,440 B2 | 6/2015 | Kuyu et al. |
| 9,095,424 B2 | 8/2015 | Kahook et al. |
| 9,097,840 B2 | 8/2015 | Chang et al. |
| 9,125,736 B2 | 9/2015 | Kahook et al. |
| 9,198,572 B2 | 12/2015 | Dai et al. |
| 2001/0037001 A1 | 11/2001 | Muller et al. |
| 2001/0056165 A1 * | 12/2001 | Mentak ............... 526/319 |
| 2002/0072795 A1 | 6/2002 | Green |
| 2002/0086160 A1 | 7/2002 | Qiu et al. |
| 2002/0102415 A1 | 8/2002 | Valint, Jr. |
| 2002/0103536 A1 | 8/2002 | Landreville et al. |
| 2002/0107568 A1 | 8/2002 | Zadno-azizi et al. |
| 2002/0111678 A1 | 8/2002 | Zadno-azizi et al. |
| 2002/0116057 A1 | 8/2002 | Ting et al. |
| 2002/0116058 A1 | 8/2002 | Zadno-azizi et al. |
| 2002/0116059 A1 | 8/2002 | Zadno-azizi et al. |
| 2002/0116060 A1 | 8/2002 | Nguyen et al. |

(56) References Cited

U.S. PATENT DOCUMENTS

| | | |
|---|---|---|
| 2002/0116061 A1 | 8/2002 | Zadno-azizi et al. |
| 2002/0138141 A1 | 9/2002 | Zadno-azizi et al. |
| 2002/0173847 A1 | 11/2002 | Pham et al. |
| 2002/0197414 A1 | 12/2002 | Chabrecek et al. |
| 2003/0008063 A1 | 1/2003 | Chabrecek et al. |
| 2003/0074060 A1 | 4/2003 | Zadno-azizi et al. |
| 2003/0074061 A1 | 4/2003 | Pham et al. |
| 2003/0078656 A1 | 4/2003 | Nguyen |
| 2003/0078657 A1 | 4/2003 | Zadno-azizi et al. |
| 2003/0078658 A1 | 4/2003 | Zadno-azizi et al. |
| 2003/0100666 A1 | 5/2003 | Degroot et al. |
| 2003/0158560 A1* | 8/2003 | Portney ............... 606/107 |
| 2003/0162929 A1 | 8/2003 | Verbruggen et al. |
| 2003/0224185 A1 | 12/2003 | Valint, Jr. |
| 2004/0111152 A1 | 6/2004 | Kelman |
| 2004/0166232 A1 | 8/2004 | Kunzler et al. |
| 2004/0230300 A1 | 11/2004 | Bandhauer et al. |
| 2005/0013842 A1 | 1/2005 | Qiu et al. |
| 2005/0049700 A1 | 3/2005 | Zadno-azizi et al. |
| 2005/0055092 A1 | 3/2005 | Nguyen et al. |
| 2005/0153055 A1 | 7/2005 | Ammon, Jr. et al. |
| 2005/0165410 A1 | 7/2005 | Zadno-azizi et al. |
| 2005/0228120 A1 | 10/2005 | Hughes et al. |
| 2005/0228401 A1 | 10/2005 | Zadno-azizi et al. |
| 2006/0069432 A1* | 3/2006 | Tran ............... 623/6.41 |
| 2006/0100703 A1 | 5/2006 | Evans et al. |
| 2006/0116765 A1 | 6/2006 | Blake et al. |
| 2006/0178741 A1 | 8/2006 | Zadno-azizi et al. |
| 2006/0241752 A1 | 10/2006 | Israel |
| 2006/0259139 A1 | 11/2006 | Zadno-azizi et al. |
| 2006/0271187 A1 | 11/2006 | Zadno-azizi et al. |
| 2007/0027540 A1 | 2/2007 | Zadno-azizi et al. |
| 2007/0050025 A1 | 3/2007 | Nguyen et al. |
| 2007/0088433 A1 | 4/2007 | Esch et al. |
| 2007/0092830 A1 | 4/2007 | Lai et al. |
| 2007/0106377 A1 | 5/2007 | Smith et al. |
| 2007/0108643 A1 | 5/2007 | Zadno-azizi et al. |
| 2007/0122540 A1 | 5/2007 | Salamone et al. |
| 2007/0203317 A1 | 8/2007 | Verbruggen et al. |
| 2007/0232755 A1 | 10/2007 | Matsushita et al. |
| 2007/0269488 A1 | 11/2007 | Ravi |
| 2008/0001318 A1 | 1/2008 | Schorzman et al. |
| 2008/0003259 A1 | 1/2008 | Salamone et al. |
| 2008/0003261 A1 | 1/2008 | Schorzman et al. |
| 2008/0015689 A1 | 1/2008 | Esch et al. |
| 2008/0046074 A1 | 2/2008 | Smith et al. |
| 2008/0076897 A1 | 3/2008 | Kunzler et al. |
| 2008/0139769 A1 | 6/2008 | Iwamoto et al. |
| 2008/0143958 A1 | 6/2008 | Medina et al. |
| 2008/0181931 A1 | 7/2008 | Qiu et al. |
| 2008/0234457 A1 | 9/2008 | Zhou et al. |
| 2008/0300680 A1 | 12/2008 | Joshua |
| 2008/0314767 A1 | 12/2008 | Lai et al. |
| 2009/0118739 A1 | 5/2009 | Kappelhof et al. |
| 2009/0143499 A1 | 6/2009 | Chang et al. |
| 2009/0168012 A1 | 7/2009 | Linhardt et al. |
| 2009/0170976 A1 | 7/2009 | Huang et al. |
| 2009/0171459 A1 | 7/2009 | Linhardt et al. |
| 2009/0232871 A1 | 9/2009 | Hitz et al. |
| 2009/0247661 A1 | 10/2009 | Muller-lierheim et al. |
| 2010/0119744 A1 | 5/2010 | Yokoyama et al. |
| 2010/0120938 A1 | 5/2010 | Phelan et al. |
| 2010/0120939 A1 | 5/2010 | Phelan |
| 2010/0121444 A1 | 5/2010 | Ben Nun |
| 2010/0160482 A1 | 6/2010 | Nachbaur |
| 2010/0179653 A1 | 7/2010 | Argento et al. |
| 2010/0211170 A1 | 8/2010 | Liao |
| 2010/0239633 A1 | 9/2010 | Strome et al. |
| 2011/0009519 A1 | 1/2011 | Awasthi et al. |
| 2011/0046332 A1 | 2/2011 | Breiner et al. |
| 2011/0118379 A1 | 5/2011 | Tighe et al. |
| 2011/0118834 A1* | 5/2011 | Lo ............... A61F 2/1635 351/159.68 |
| 2011/0133350 A1 | 6/2011 | Qiu et al. |
| 2011/0140292 A1 | 6/2011 | Chang et al. |
| 2011/0144228 A1 | 6/2011 | Ravi |
| 2011/0269869 A1 | 11/2011 | Medina et al. |
| 2011/0282442 A1 | 11/2011 | Scholl et al. |
| 2011/0295368 A1 | 12/2011 | Betser |
| 2012/0010321 A1 | 1/2012 | Chang et al. |
| 2012/0023869 A1 | 2/2012 | Samuel et al. |
| 2012/0033183 A1 | 2/2012 | Dai et al. |
| 2012/0041097 A1 | 2/2012 | Zhou et al. |
| 2012/0046743 A1 | 2/2012 | Pinchuk |
| 2012/0078363 A1 | 3/2012 | Lu |
| 2012/0078364 A1 | 3/2012 | Stenger |
| 2012/0088843 A1 | 4/2012 | Chang et al. |
| 2012/0088844 A1 | 4/2012 | Kuyu et al. |
| 2012/0088861 A1 | 4/2012 | Huang et al. |
| 2012/0115979 A1 | 5/2012 | Chang et al. |
| 2012/0147323 A1 | 6/2012 | Domschke |
| 2012/0245684 A1 | 9/2012 | Liao |
| 2012/0314183 A1 | 12/2012 | Nakamura et al. |
| 2012/0330415 A1 | 12/2012 | Callahan et al. |
| 2013/0013060 A1 | 1/2013 | Zadno-azizi et al. |
| 2013/0095235 A1 | 4/2013 | Bothe et al. |
| 2013/0106007 A1 | 5/2013 | Medina et al. |
| 2013/0110234 A1 | 5/2013 | Devita et al. |
| 2013/0116781 A1 | 5/2013 | Ben Nun |
| 2013/0150961 A1 | 6/2013 | Evans et al. |
| 2013/0197125 A1 | 8/2013 | Awasthi et al. |
| 2013/0224309 A1 | 8/2013 | Qiu et al. |
| 2013/0228943 A1 | 9/2013 | Qiu et al. |
| 2013/0245756 A1 | 9/2013 | Liao |
| 2013/0289294 A1 | 10/2013 | Awasthi et al. |
| 2013/0304203 A1 | 11/2013 | Beer |
| 2014/0055750 A1 | 2/2014 | Dai et al. |
| 2014/0171539 A1 | 6/2014 | Chang et al. |
| 2014/0171542 A1 | 6/2014 | Chang |
| 2014/0178595 A1 | 6/2014 | Bothe et al. |
| 2014/0180403 A1 | 6/2014 | Silvestrini et al. |
| 2014/0228949 A1 | 8/2014 | Argento et al. |
| 2014/0277439 A1 | 9/2014 | Hu et al. |
| 2014/0309735 A1 | 10/2014 | Sohn et al. |
| 2014/0350124 A1 | 11/2014 | Kuyu et al. |
| 2014/0379079 A1 | 12/2014 | Ben Nun |
| 2015/0092155 A1 | 4/2015 | Chang et al. |
| 2015/0152228 A1 | 6/2015 | Chang et al. |
| 2015/0177417 A1 | 6/2015 | Nakamura et al. |
| 2015/0351901 A1 | 12/2015 | Stoy et al. |

FOREIGN PATENT DOCUMENTS

| | | |
|---|---|---|
| EP | 0734269 A1 | 10/1996 |
| EP | 0784652 A1 | 7/1997 |
| EP | 0800511 A1 | 10/1997 |
| EP | 0820601 A1 | 1/1998 |
| EP | 0826158 A1 | 3/1998 |
| EP | 0898972 A2 | 3/1999 |
| EP | 0907668 A1 | 4/1999 |
| EP | 0930357 A1 | 7/1999 |
| EP | 0604369 B1 | 8/1999 |
| EP | 0826158 B1 | 9/1999 |
| EP | 0947856 A2 | 10/1999 |
| EP | 0820601 B1 | 12/1999 |
| EP | 0800511 B1 | 1/2000 |
| EP | 0989138 A2 | 3/2000 |
| EP | 1084428 A1 | 3/2001 |
| EP | 1088246 A1 | 4/2001 |
| EP | 1090313 A1 | 4/2001 |
| EP | 1095711 A2 | 5/2001 |
| EP | 1095965 A1 | 5/2001 |
| EP | 1095966 A2 | 5/2001 |
| EP | 1109853 A1 | 6/2001 |
| EP | 0907668 B1 | 9/2001 |
| EP | 1141054 A1 | 10/2001 |
| EP | 1187873 A1 | 3/2002 |
| EP | 1200019 A1 | 5/2002 |
| EP | 1227773 A1 | 8/2002 |
| EP | 1230041 A2 | 8/2002 |
| EP | 1266246 A1 | 12/2002 |
| EP | 0898972 B1 | 4/2003 |
| EP | 1341485 A1 | 9/2003 |
| EP | 1364663 A1 | 11/2003 |

(56) References Cited

FOREIGN PATENT DOCUMENTS

| | | |
|---|---|---|
| EP | 1095711 B1 | 1/2004 |
| EP | 1141054 B1 | 2/2004 |
| EP | 1395302 A1 | 3/2004 |
| EP | 1410074 A1 | 4/2004 |
| EP | 1266246 B1 | 6/2004 |
| EP | 1109853 B1 | 9/2004 |
| EP | 1187873 B1 | 9/2004 |
| EP | 1084428 B1 | 11/2004 |
| EP | 1472305 A1 | 11/2004 |
| EP | 1230041 B1 | 12/2004 |
| EP | 0989138 B1 | 2/2005 |
| EP | 1095965 B1 | 2/2005 |
| EP | 1395302 B1 | 2/2005 |
| EP | 1507811 A1 | 2/2005 |
| EP | 1524953 A2 | 4/2005 |
| EP | 1200019 B1 | 9/2005 |
| EP | 1095966 B1 | 1/2006 |
| EP | 1660153 A2 | 5/2006 |
| EP | 1696975 A1 | 9/2006 |
| EP | 1341485 B1 | 11/2006 |
| EP | 1723933 A2 | 11/2006 |
| EP | 1723934 A2 | 11/2006 |
| EP | 1750157 A1 | 2/2007 |
| EP | 1088246 B1 | 11/2007 |
| EP | 1857477 A1 | 11/2007 |
| EP | 1227773 B1 | 1/2008 |
| EP | 1888660 A2 | 2/2008 |
| EP | 1890650 A2 | 2/2008 |
| EP | 1902737 A1 | 3/2008 |
| EP | 1723933 B1 | 11/2008 |
| EP | 2035050 A2 | 3/2009 |
| EP | 2035480 A1 | 3/2009 |
| EP | 2035486 A1 | 3/2009 |
| EP | 1723934 B1 | 6/2009 |
| EP | 2066732 A2 | 6/2009 |
| EP | 2077292 A1 | 7/2009 |
| EP | 2092376 A1 | 8/2009 |
| EP | 1353611 B1 | 9/2009 |
| EP | 1648534 B1 | 9/2009 |
| EP | 2094193 A2 | 9/2009 |
| EP | 2109784 A1 | 10/2009 |
| EP | 2120789 A2 | 11/2009 |
| EP | 2126614 A2 | 12/2009 |
| EP | 2035480 B1 | 2/2010 |
| EP | 2170708 A2 | 4/2010 |
| EP | 2185589 A2 | 5/2010 |
| EP | 2231207 A1 | 9/2010 |
| EP | 1750157 B1 | 10/2010 |
| EP | 2235094 A1 | 10/2010 |
| EP | 2276513 A2 | 1/2011 |
| EP | 2292672 A2 | 3/2011 |
| EP | 2356170 A1 | 8/2011 |
| EP | 2356497 A2 | 8/2011 |
| EP | 2109784 B1 | 10/2011 |
| EP | 2396355 A2 | 12/2011 |
| EP | 2035486 B1 | 4/2012 |
| EP | 2452212 A2 | 5/2012 |
| EP | 1857477 B1 | 6/2012 |
| EP | 1410074 B1 | 10/2012 |
| EP | 2092376 B1 | 10/2012 |
| EP | 2510051 A1 | 10/2012 |
| EP | 2513711 A1 | 10/2012 |
| EP | 2514791 A1 | 10/2012 |
| EP | 2356170 B1 | 12/2012 |
| EP | 2538266 A1 | 12/2012 |
| EP | 2597113 A1 | 5/2013 |
| EP | 2598936 A1 | 6/2013 |
| EP | 2077292 B1 | 8/2013 |
| EP | 2625216 A1 | 8/2013 |
| EP | 2625217 A1 | 8/2013 |
| EP | 2625218 A1 | 8/2013 |
| EP | 2652532 A1 | 10/2013 |
| EP | 1830898 B1 | 3/2014 |
| EP | 2766750 A1 | 8/2014 |
| EP | 2452212 B1 | 3/2015 |
| ES | 2283058 T3 | 10/2007 |
| FR | 2653325 A1 | 4/1991 |
| WO | WO 90/07545 A2 | 7/1990 |
| WO | WO 90/07575 A1 | 7/1990 |
| WO | WO 95/16475 A1 | 6/1995 |
| WO | WO 96/36890 A1 | 2/1996 |
| WO | WO 96/11235 A1 | 4/1996 |
| WO | WO 96/20919 A1 | 7/1996 |
| WO | WO 96/31791 A1 | 10/1996 |
| WO | WO 97/49740 A1 | 6/1997 |
| WO | WO 99/17684 A1 | 4/1999 |
| WO | WO 99/29818 A1 | 6/1999 |
| WO | WO 99/57581 A1 | 11/1999 |
| WO | WO 99/60428 A1 | 11/1999 |
| WO | WO 99/63366 A1 | 12/1999 |
| WO | WO 00/04078 A1 | 1/2000 |
| WO | WO 00/35980 A1 | 6/2000 |
| WO | WO 00/71613 A1 | 11/2000 |
| WO | WO 01/08607 A1 | 2/2001 |
| WO | WO 01/34067 A1 | 3/2001 |
| WO | WO 01/30512 A2 | 5/2001 |
| WO | WO 01/71392 A1 | 9/2001 |
| WO | WO 02/47583 A1 | 6/2002 |
| WO | WO 02/094331 A1 | 11/2002 |
| WO | WO 03/009014 A1 | 1/2003 |
| WO | WO 03/066707 A1 | 8/2003 |
| WO | WO 03/097711 A1 | 11/2003 |
| WO | WO 2004/010905 A2 | 2/2004 |
| WO | WO 2004/054471 A1 | 3/2004 |
| WO | WO 2004/046768 A2 | 6/2004 |
| WO | WO 2004/052242 A1 | 6/2004 |
| WO | WO 2004/053536 A2 | 6/2004 |
| WO | WO 2004/058318 A1 | 7/2004 |
| WO | WO 2004/072689 A2 | 8/2004 |
| WO | WO 2005/023331 A2 | 3/2005 |
| WO | WO 2005/065734 A1 | 7/2005 |
| WO | WO 2006/047383 A2 | 5/2006 |
| WO | WO 2006/103674 A2 | 10/2006 |
| WO | WO 2006/126095 A2 | 11/2006 |
| WO | WO 2007/005778 A2 | 1/2007 |
| WO | WO 2007/047529 A2 | 4/2007 |
| WO | WO 2007/047530 A2 | 4/2007 |
| WO | WO 2007/050394 A2 | 5/2007 |
| WO | WO 2007/064594 A2 | 6/2007 |
| WO | WO 2008/005644 A1 | 1/2008 |
| WO | WO 2008/005652 A1 | 1/2008 |
| WO | WO 2008/005752 A2 | 1/2008 |
| WO | WO 2008/024766 A2 | 2/2008 |
| WO | WO 2008/039655 A2 | 4/2008 |
| WO | WO 2008/076729 A1 | 6/2008 |
| WO | WO 2008/077040 A2 | 6/2008 |
| WO | WO 2008/082957 A2 | 7/2008 |
| WO | WO 2008/094876 A1 | 8/2008 |
| WO | WO 2008/103798 A2 | 8/2008 |
| WO | WO 2008/107882 A2 | 9/2008 |
| WO | WO 2008/116132 A2 | 9/2008 |
| WO | WO 2008/151088 A2 | 12/2008 |
| WO | WO 2009/002703 A2 | 12/2008 |
| WO | WO 2009/015161 A2 | 1/2009 |
| WO | WO 2009/015226 A2 | 1/2009 |
| WO | WO 2009/015234 A2 | 1/2009 |
| WO | WO 2009/015240 A2 | 1/2009 |
| WO | WO 2009/085755 A1 | 7/2009 |
| WO | WO 2009/085756 A1 | 7/2009 |
| WO | WO 2009/127844 A2 | 10/2009 |
| WO | WO 2010/056686 A1 | 5/2010 |
| WO | WO 2010/056687 A2 | 5/2010 |
| WO | WO 2010/081093 A2 | 7/2010 |
| WO | WO 2010/093823 A2 | 8/2010 |
| WO | WO 2011/005937 A2 | 1/2011 |
| WO | WO 2011/026068 A2 | 3/2011 |
| WO | WO 2011/071790 A1 | 6/2011 |
| WO | WO 2011/075377 A1 | 6/2011 |
| WO | WO 2011/106435 A2 | 9/2011 |
| WO | WO 2012/006616 A2 | 1/2012 |
| WO | WO 2012/015639 A1 | 2/2012 |
| WO | WO 2012/047961 A1 | 4/2012 |
| WO | WO 2012/047964 A1 | 4/2012 |
| WO | WO 2012/047969 A1 | 4/2012 |

(56) References Cited

FOREIGN PATENT DOCUMENTS

| WO | WO 2012/082704 A1 | 6/2012 |
|---|---|---|
| WO | WO 2012/129407 A2 | 9/2012 |
| WO | WO 2013/055746 A1 | 4/2013 |
| WO | WO 2013/070924 A1 | 5/2013 |
| WO | WO 2013/158942 A1 | 10/2013 |
| WO | WO 2013/166068 A1 | 11/2013 |
| WO | WO 2014/093751 A2 | 6/2014 |
| WO | WO 2014/093764 A1 | 6/2014 |
| WO | WO 2014/095690 A1 | 6/2014 |
| WO | WO 2014/143926 A1 | 9/2014 |
| WO | WO 2014/149462 A1 | 9/2014 |
| WO | WO 2014/152017 A1 | 9/2014 |
| WO | WO 2015/038620 A2 | 3/2015 |
| WO | WO 2015/048279 A1 | 4/2015 |
| WO | WO-2015066502 A1 | 5/2015 |
| WO | WO 2015/148673 A1 | 10/2015 |

OTHER PUBLICATIONS

Klank, et al. CO2-laser micromachining and back-end processing for rapid production of PMMA-based microfluidic systems. Lab Chip, 2002, 2, 242-246.
Tsao, et al. Bonding of thermoplastic polymer microfluidics. Microfluid Nanofuild (2009) 6:1-16.
Umbrecht, et al. Solvent assisted bonding of polymethylmethacrylate: characterization using the response surface methodology. pp. 1325-1328.
International search report and written opinion dated Nov. 30, 2015 for PCT/US2015/046998.
U.S. Appl. No. 14/836,646, filed Aug. 26, 2015, Salahieh et al.
Co-pending U.S. Appl. No. 14/860,162, filed Sep. 21, 2015.

* cited by examiner

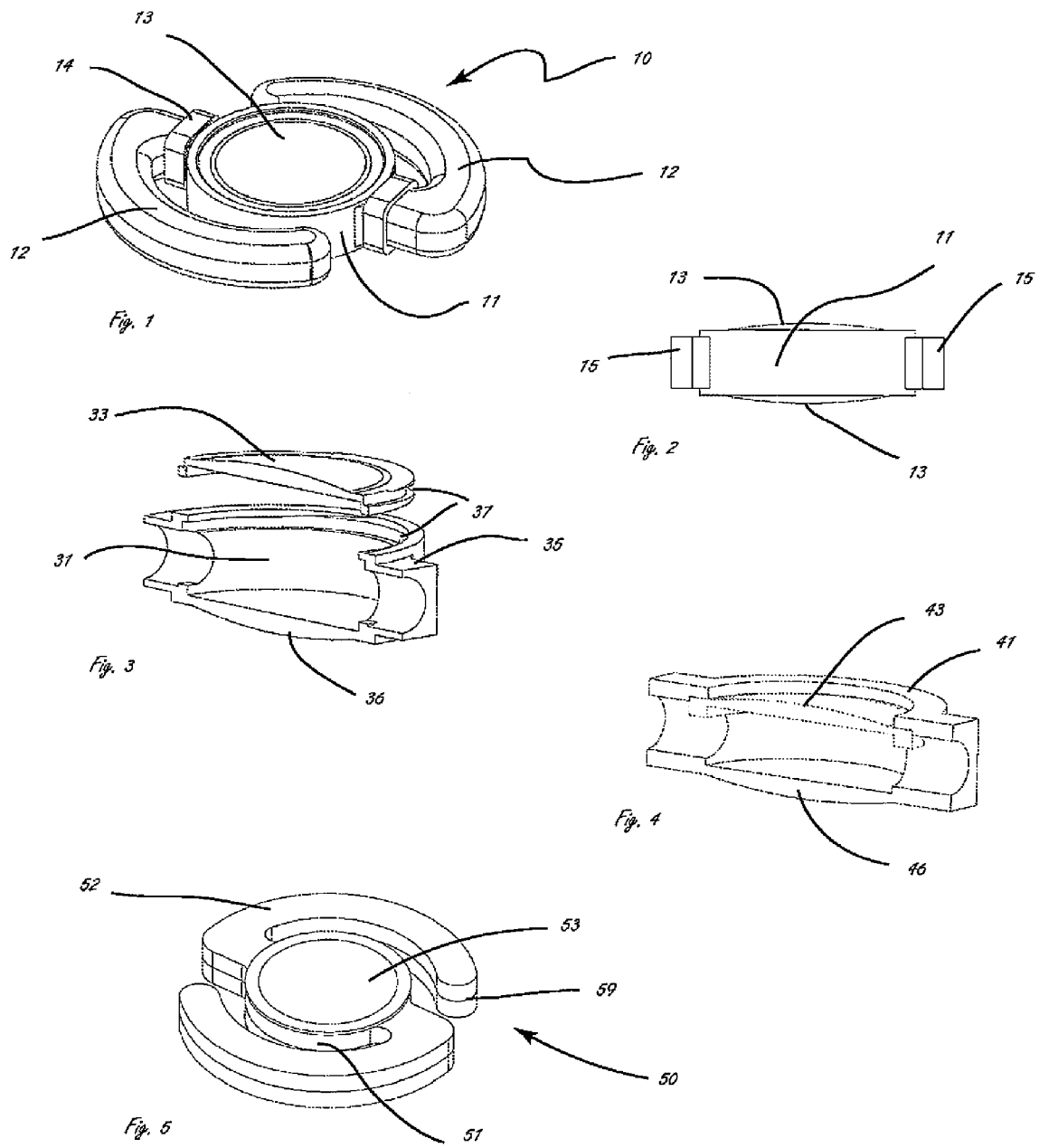

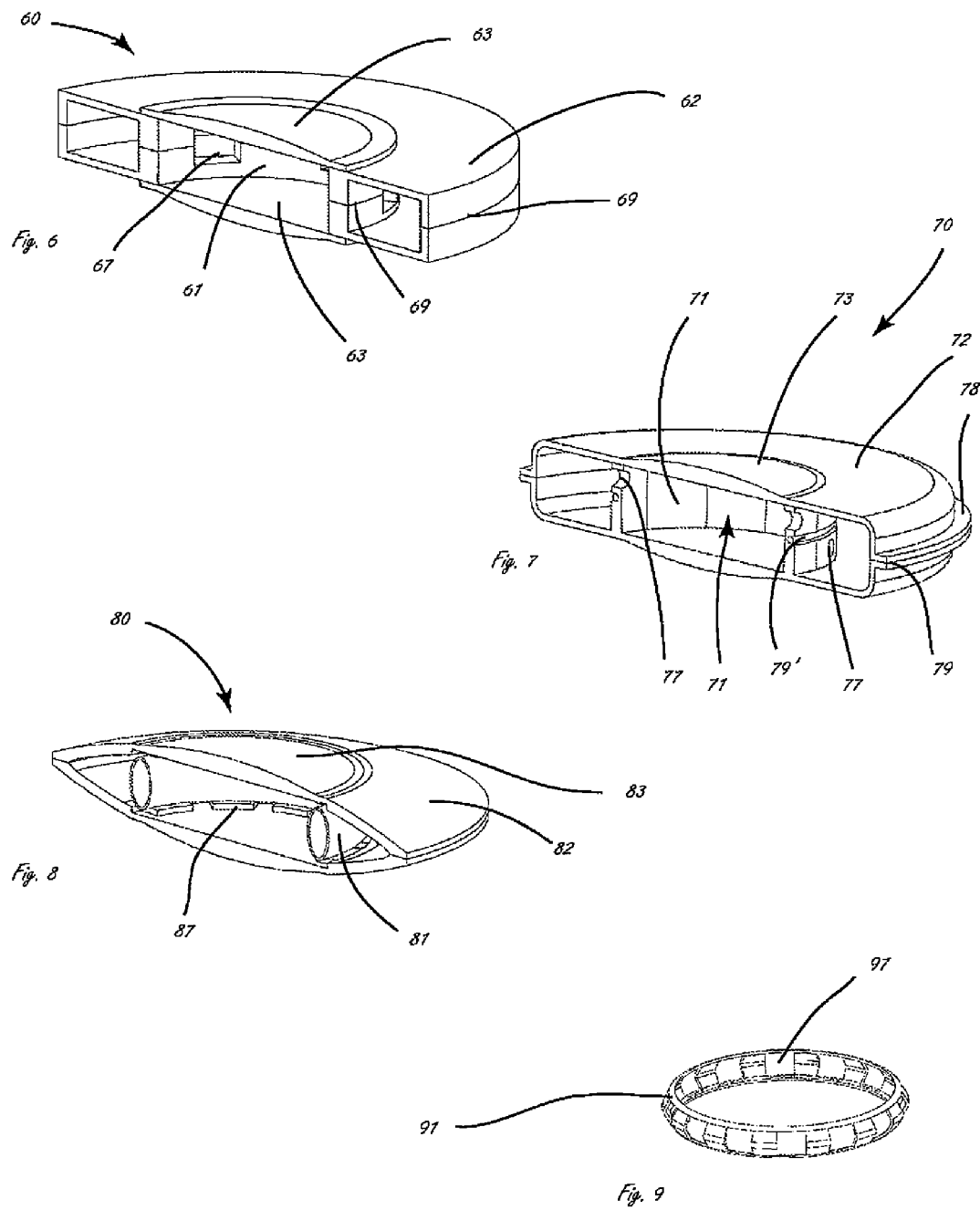

HYDROPHILIC AIOL WITH BONDING

CROSS-REFERENCE

This application is related to the following co-pending provisional patent applications: application Ser. No. 61/764,699, filed on Feb. 14, 2013, entitled "Hydrophilic AIOL"; and application Ser. No. 61/764,715 filed on Feb. 14, 2013; the entire disclosures of which are incorporated herein by reference.

BACKGROUND

The eye is critical for vision. As people age, the crystalline lens of the eye may move less than ideally, a condition referred to as presbyopia. For presbyopes with good distance vision, reading glasses may be required for near vision. Although multifocal lenses can be helpful, such lenses can provide more than one focal point of the eye and provide less than ideal vision. As the eye ages further, the crystalline lens may have cataracts that degrade vision, requiring removal of the crystalline lens and replacement with an intraocular lens. Although intraocular lenses can be helpful to restore vision, such lenses may not restore accommodation and in many instances provide a fixed focal length of the eye.

Although accommodating intra ocular lenses (hereinafter "AIOLs" or "accommodating IOL") have been proposed, the prior AIOLs can provide less than ideal results in at least some instances. At least some of the prior AIOLs provide less than ideal amounts of accommodation. Also, as the amount of force of the capsular bag can be somewhat less than ideal, at least some of the prior IOLs may provide less than ideal amounts of accommodation in response to the forces of the capsular bag. Further, work in relation to embodiments suggests that the prior AIOLs may be less than ideally suited for insertion into the eye in at least some instances. Clinically, an incision that is larger than ideal may result in astigmatism of the eye, and it would be helpful if an accommodating IOL could be inserted through small incision. Also, the prior AIOLs can be somewhat more difficult to manufacture than would be ideal. AIOLs to correct vision can be machined to very accurate tolerances, and soft materials can be more difficult to machine than would be ideal in at least some instances. Also, work in relation to embodiments suggests that prior methods and apparatus of bonding AIOLs can be less than ideal.

For the above reasons, improved AIOLs, and methods of manufacture and use are needed.

SUMMARY

Embodiments of the present disclosure provide improved accommodating IOL methods and apparatus. In many embodiments, an accommodating IOL comprises a first lens component and a second lens component each composed of a polymer, and adhesive comprising the polymer. In many embodiments, the polymer can be hydrated and swells with hydration, such that the first component, the second component, and the adhesive swell together (e.g., at the same or substantially similar rate). By swelling together, stresses among the first component, the second component, and the adhesive can be inhibited substantially. Also, the hydratable adhesive allows the first and second components to be machined in a stiff less than fully hydrated configuration prior to adhering of the components together. The stiff configuration may comprise a less than fully hydrated polymer, such as a substantially dry polymer. The components can be bonded together in the stiff substantially configuration to facilitate handling during manufacturing, and subsequently hydrated such that the components bonded the adhesive comprise a soft hydrated configuration for insertion into the eye. The adhesive comprising the polymer can bond the first and second lens components together with chemical bonds similar to the polymer material itself in order to provide increased strength.

The first component comprises a first disk shaped structure and the second component comprises a second disc shaped structure. An annular structure extends between the first disc shaped structure and the second disc shaped structure to define a chamber containing a fluid having an index of refraction greater than about 1.336, which is the index of refraction of the aqueous humor of the eye. When one or more of the first disk structure or the second disk structure increases in curvature, optical power of the IOL increases. The adhesive can bond the first component to the second component by extending circumferentially around one or more of the annular structure, the first disc shaped component, the second disc shaped component, and combinations thereof. In many embodiments, the adhesive is located in a seam extending circumferentially around the one or more of the annular structure, the first disc shaped component, the second disc shaped component, and combinations thereof, which bonds the components together. Locating the seam away from the optical portions of the first and second components provides improved optical properties. Also, the adhesive comprising the polymer of the first and second components swells similarly to the first and second components, and can be particularly helpful when provided circumferentially around the first and second component, as these components can swell substantially along the diameter. Decreasing stresses along bonds of an accommodating IOL can be particularly helpful as the IOL can be made smaller to decrease insertion size and may comprise thin deformable structures configured to deform with decreased stresses.

In many embodiments, the first and second components are machined on a lathe to provide rotationally symmetric structures, such as the first disc shaped structure and the second disc shaped structure. One or more of the first component or the second component may comprise the annular structure prior to bonding the components together. One or more annular grooves can be provided on the first component and the second component in order to align optically the first component with the second component. The adhesive can be placed in the groove and cured when the first component and the second component comprise the stiff substantially dry configuration.

In many embodiments, the adhesive comprises a prepolymer of the polymer of the components. The prepolymer may comprise one or more of a monomer, an oligomer, a partially cured monomer, particles, or nano particles of the polymer.

The accommodating IOL may comprise one or more haptics to couple the disc shaped components to the capsular bag in order to change the optical power of the lens in response to deformations of the capsular bag. In many embodiments, the one or more haptics comprise chambers fluidically coupled to the chamber comprising the first and second lens components. The haptics can be made of a soft material such as a silicone, for example.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1 illustrates a perspective view of an accommodating intra ocular lens system, in accordance with many embodiments;

FIG. 2 illustrates a side view of a lens support structure and lens, in accordance with many embodiments;

FIG. 3 illustrates a sectioned view of a lens support structure incorporating a lens interfaced using threads, in accordance with many embodiments;

FIG. 4 illustrates a sectioned view of a lens support structure incorporating a lens interfaced using an interference fit, in accordance with embodiments;

FIG. 5 illustrates a perspective view of an alternative accommodating intra ocular lens system, in accordance with many embodiments;

FIG. 6 illustrates a sectioned view of an alternative accommodating intra ocular lens system, in accordance with many embodiments;

FIG. 7 illustrates a sectioned view of an alternative accommodating intra ocular lens system, in accordance with many embodiments;

FIG. 8 illustrates a sectioned view of an alternative accommodating intra ocular lens system, in accordance with many embodiments;

FIG. 9 shows a perspective view of a support structure for the AIOL of FIG. 8, in accordance with alternate embodiments of the AIOL of FIG. 8;

DETAILED DESCRIPTION

Figure 10:
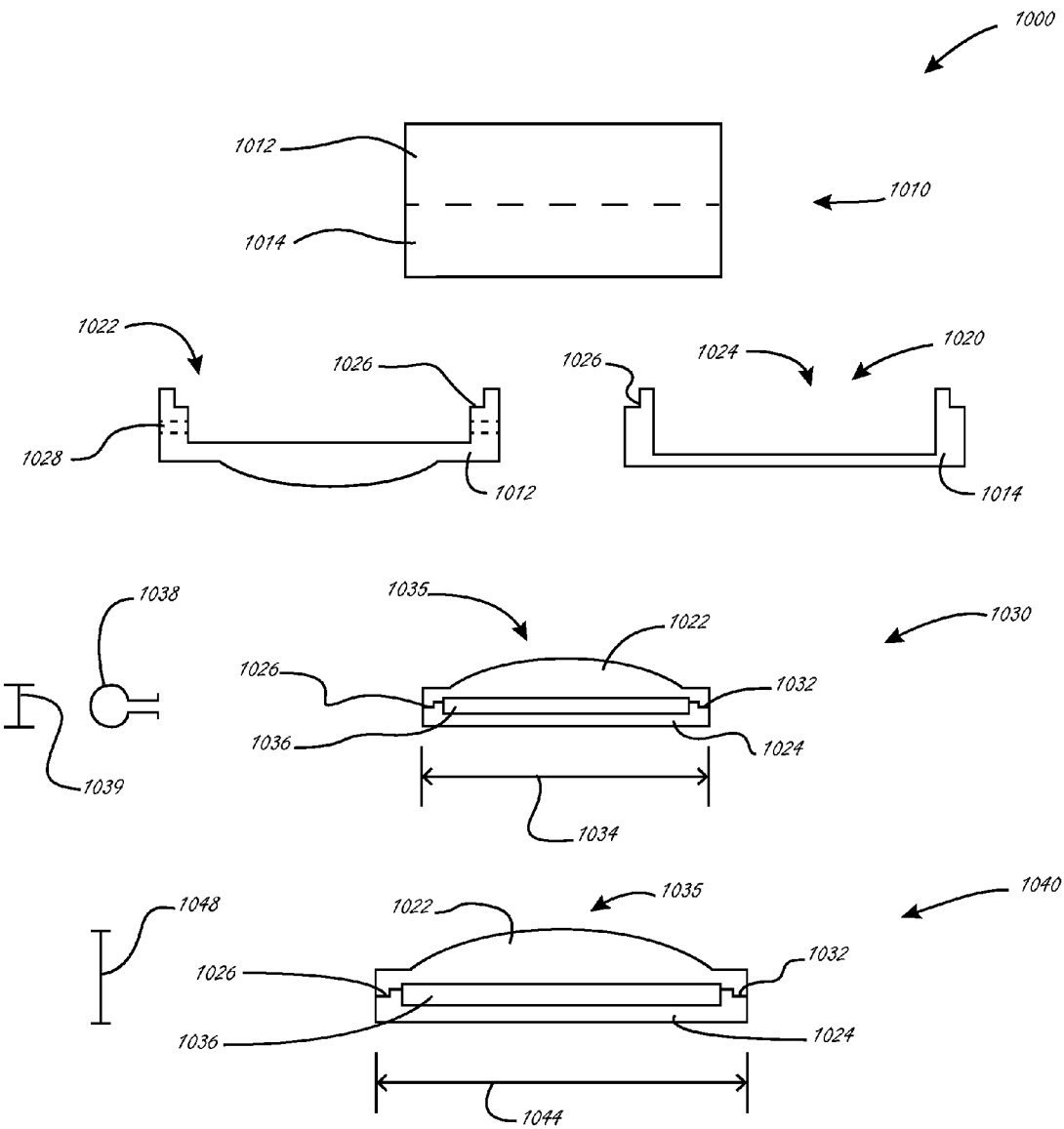
FIG. 10 shows a method of manufacturing an AIOL, in accordance with many embodiments.

In many embodiments, an accommodating intra ocular lens system (AIOL) comprises a central structure comprising two deformable lenses spaced apart along their optical axis by an outer support structure concentric with the optical axis of the lenses. The volume bounded by the lenses and the outer support structure may be filled with a fluid, such as an ionic solution (saline). Alternatively or in combination, other fluids can be used such as oil, silicone oil, or solutions comprising high molecular weight molecules such as high molecular weight dextran solution, for example. In such solutions of high molecular weight materials, the solute may increase the refractive index while the high molecular weight of the solute may inhibit the diffusion of the solute from the inner chamber. The outer support structure in turn may be bounded by one or more fluid filled haptics arranged in a plane normal to the optical axis of the lenses. The haptics may be in fluid communication with the fluid bounded by the inner support structure. The transfer of fluid between the haptics and the fluid filled support structure may change the accommodating power of the lens system. The system as described herein may additionally comprise any or any combination of the following features:

A reduced delivery cross section is facilitated by an internal support structure capable of translating from a delivery configuration to an operational configuration. The inner support structure may have a small dimension along the optical axis in the delivery configuration and larger dimension along the optical axis in operational configuration. The inner support structure may be designed to maintain the distance between the periphery of the two lenses in the operational configuration and to allow fluid to pass between the haptics and the volume bounded by the internal support structure.

The delivery cross section can be attained by folding or rolling the AIOL around a delivery axis normal to the optical axis. The delivery cross section may be measured as the largest dimension in the delivery configuration measured in a plane normal to the delivery axis. Delivery cross sections attainable for the AIOLS described herein may be less than 4.5 mm, and preferably less than 2.5 mm.

The lens system may comprise of at least two hydrophilic PMMA lenses, and may include other elements comprising any or any combination of the following materials: NiTi, poly urethane, hydrophilic PMMA, photo activated polymers, precursors to PMMA, poly(hydroxy ethyl) methacrylate (PHEMA), copolymers of polymethyl methacrylate and PHEMA, and Ethylene glycol dimethylacrylate.

In some embodiments, the internal support structure comprises a material which is changed from a delivery configuration to an operation configuration after introduction into the capsule of the eye. One such material comprises a photo active polymer which in the delivery configuration may be a liquid which can be hardened by photo activation after introduction. Another such material comprises a memory metal such as an NiTi alloy which in the delivery configuration may have a thin dimension in a plane normal to the optical axis and after introduction may be initiated to change to an operational configuration by heating via inductive coupling or body heat, alternatively or in combination.

The internal support structure in some embodiments is mechanically more stable in the operational configuration than in the delivery configuration, and spontaneously changes from a delivery configuration to an operational configuration after introduction into the capsule of the eye. In such a configuration the internal support structure may be coaxed into a delivery configuration just prior to delivery or at manufacture.

One such system comprises a super elastic metal element which springs from the delivery configuration upon introduction of the device into the capsule.

In some embodiments, the inner support structure and one lens are machined or molded as a single structure and the second lens is affixed to the support structure by an alternate means. Alternate means include mechanical interfaces such as threading where the outer periphery of the lens is threaded and the inner surface of the support structure is threaded. In an alternate embodiment, the interface can be a simple interference fit. In some embodiments, affixing comprises bonding the materials by treating the one or both of the separate bonding surfaces with a precursor monomer, then assembling the structure, applying a load across the bonding surfaces, and heating the assembly for a period of time.

In the devices of the present disclosure, the lenses may comprise a water and ion permeable material. In some embodiments, the AIOL is allowed to self fill after implantation, thereby minimizing the delivery cross section.

In an alternate embodiment, the AIOL is filled after implant.

The lenses and some of the support structures described herein are fabricated from a hydrophilic material such as a copolymer of hydroxyethyl methacrylate and methyl methacrylate such as CI18, CI21, or CI26 produced by Contamac Ltd. of the UK. These materials are optically clear when hydrated, swell on hydration by more than 10% (for example, by 10-15%), and accommodate strain levels of greater than 100% when hydrated. When fully hydrated, these materials may have a water content of 15 to 30%. For example, CI18 when fully hydrated may be composed of 18% water, CI21 when fully hydrated may be composed of 21% water, and CI26 when fully hydrated may be composed of 26% water. In a substantially dry state or configuration, these materials may be have a water content of no more than about 5%, for example 0.2-3%. These materials are often oven dried prior to machining.

FIG. 1 illustrates an accommodating intraocular lens system 10 which may comprise a central lens support structure 11, two haptics 12, two deformable lenses 13 of which only one is visible in the figure, and two compression bands 14. The haptics may comprise thin walled structures configured to deform under minimal loads and comprise an elastomeric material. The internal volume of the AIOL can be filled with a clear fluid such as saline of comparable osmolality to that of the fluids in the eye around the lens capsule. The lenses 13 may be interfaced to the support structure 11 such that as fluid transfers from the haptics into the internal volume of the support structure the lenses are caused to deform thereby changing their accommodative power. A side view of the lens support structure 11 of FIG. 1 along with two lenses 13 is illustrated in FIG. 2. Also visible in FIG. 2 are the haptic interface features 15 comprised in the lens support structure 11. The open end of the haptics 12 may fit over the haptic interface features 15 and may be further affixed to the lens support structure interface feature 15 using compression bands 14. Additionally, in some embodiments, an adhesive or sealant may be used. The distance between the periphery of the lens can be maintained by the support structure while the centre of the lens may be allowed to deform as the fluid volume within the support structure increases, thereby changing the accommodative power of the structure.

FIG. 3 illustrates a lens support structure in which one of the two lenses, lens 36 is comprised in the support structure. The second lens in the embodiment of FIG. 3 may be designed to interface to the support structure via threads 37. Another embodiment for a central support structure similar to that of FIG. 3 is illustrated in FIG. 4. In this embodiment, the second lens 43 may be interfaced via an interference fit. In some embodiment, the interference fit may be further sealed through the use of a sealant or adhesive. The interference fit may be further facilitated by the procedure used to assemble and rehydrate the components. One such procedure as implemented on the structure of FIG. 4 may be as follows: the bottom of the support structure 41 comprising lens 46 may be hydrated, the lens 43 in the unhydrated condition can then be fitted into the groove comprised in the support structure 41, the support structure and lenses may be allowed to completely hydrate, and, if required, a sealant or adhesive may then be applied. The use of interference fits can minimize the requirement and or amount of bonding agent.

FIG. 5 illustrates another embodiment of an AIOL 50 in which half of the support structure 41 and haptics 42 may be comprised in an upper and lower half of the AIOL 50 and thereby all fabricated from the same material. The two halves may be bonded together at seam 59 to form the complete haptic and support structure. Lens 53 may either be integral to the half structures as or bonded to the support structure. In the manufacturing environment allowing one lens to be aligned and bonded after the fabrication of the rest of the structure provides advantage in assuring the optical axis of the two lenses are precisely aligned.

In the embodiments of FIGS. 1 and 2, the haptics are configured in such a fashion that they may be folded out and away from the support structure in a plane normal to the optical axis of the lenses. Such a configuration may facilitate a reduction in delivery cross section for a fluid filled device. In the embodiment of FIG. 6 through 7, the haptics may be both integral to the support structure and attached continuously around the perimeter of the support structure.

FIG. 6 illustrates an embodiment of an AIOL 60 wherein the haptic 62 and the support structure 61 are integral and are configured as a toroid like structure. The inner radius of the structure comprises the support structure 61. Fluid may be allowed to flow between the haptic 62 and the inner volume of the support structure 61 through openings 67. The AIOL 60 can be fabricated by bonding the two halve at seam 59. Lens 63 may be integral with the halves are bonded separately to the halves.

A variation on the embodiment of FIG. 6 is illustrated in FIG. 7. The embodiment of the AIOL 70 may incorporate features which help to reduce the delivery cross section. Half of the support structure may be comprised on each the upper and lower halves on the AIOL 70 and comprises a series of structures 71 each separated by as space forming a castellated ring. Castellated structures can be meshed at assembly prior to bonding at seam 79. Spring ring 79 may fit in a grove and may lock the upper and lower halves of the structure relative to displacements along the optical axis. As shown in FIG. 7, the lenses 73 can be integral to the half structures comprising the AIOL 70. In other embodiments, the lenses 73 may be separate and bonded at another time. In such an embodiment, the support structure is capable of greater deformation during delivery as the castellated elements can fold over a greater radius of curvature. AIOL 70 also comprises feature 78, which allows for a means of applying pressure directly across seam 79 during the bonding process.

FIG. 8 represents an embodiment of an AIOL 80 which comprises an elastomeric support structure 81 filled with a fluid capable of being hardened after delivery of the AIOL. Such fluids may be optically cured, such as a UV curing silicone or epoxy, pH cured such as a collagen solution, or heat cured where the material contains a suspension of particle capable of being inductively heated such as magnitite particles. Channels 87 may allow fluid to pass between the haptic and the central volume of the support structure.

FIG. 9 shows a support structure 81 in accordance with an alternate embodiment of AIOL 80. The support structure 81 may be replaced with a support structure 91 which comprises a memory metal which can be flattened prior to assemble then headed by inductive coupling allow it to take an operation configuration after delivery, such a configuration provides for a reduced cross section.

Embodiments described herein also allow for sequencing the assembly and the use of long setting, heat, pressure, and or optical initiated bonding materials to insure proper optical alignment of the lenses.

Bonding

Bonding can be used to bond one or more of many AIOL structures as disclosed herein.

Bonding of a copolymer of hydroxyethyl methacrylate and methyl methacrylate may be facilitated by treating the bond surfaces with an Ethylene glycol dimethylacrylate or Ethylene glycol trimethylacrylate. Then, the bonded surfaces may be subjected to pressure and temperature. Treatment may include but is not limited to vapor treatment, wetting, wetting and allowing for evaporation, applying a mixture of Ethylene glycol dimethylacrylate or Ethylene glycol trimethylacrylate and particles of a copolymer of hydroxyethyl methacrylate and methyl methacrylate.

Such a bonding scheme can provide advantage in that there is no or minimal seam—the bonded interface has the same mechanical properties as the structure.

Each of the components can be provided in a stiff configuration for machining and bonded together with the adhesive while in a stiff configuration. The component can be subsequently hydrated.

The prepolymer of the adhesive may comprise one or more of Ethylene glycol dimethylacrylate or Ethylene glycol trimethylacrylate, and the prepolymer can be cured to bond the first and second components together. The precursor monomers may be partially or fully polymerized by the addition of an initiator. The initiator may be a photoinitiator such as Irgacure 651 (I651,Ciba-Geigy), or an initiator such as 2,2'-azobis(isobutyonitrile), 2,2'-azobis(2,4-dimethylvaleronitrile), dilauroyl peroxide and bis(4-t-butylcyclohexyl) peroxydicarbonate, for example.

In many embodiments, the first and second lens components comprise a copolymer of hydroxyethyl methacrylate and methyl methacrylate. When cured, the adhesive comprises the copolymer of hydroxyethyl methacrylate and methyl methacrylate. This configuration can allow the lens to expand from a stiff less than fully hydrated configuration, to the fully hydrated configuration with substantially swelling and inhibited stress to the components and the adhesive located along the seam. The stiff, less than fully hydrated configuration of the polymer material will be understood by a person of ordinary skill in the art to comprise a polymer having a sufficiently low amount of water to provide stiffness to the polymer material of the first and second components. The less than fully hydrated configuration may comprise a substantially dry configuration composed of no more than about 5% water, for example 0.2-3% water, such that the polymer material comprises sufficient stiffness for machining the material to optical tolerances as will be readily understood by a person of ordinary skill in the art. When the AIOL is placed in the lens capsule or placed in a hydration buffer as understood by a person of ordinary skill in the art, for example, the polymer may swell to a hydrated state and gradually to a fully hydrated state. The polymer in the fully hydrated state may be composed of about 15% to 30% water, for example, depending on the material selected. The polymer in the fully hydrated state may swell by more than 10%, such as 10% to 15%.

FIG. 10 shows a method 1000 of manufacturing and providing an AIOL.

At a step 1010, a block of polymer material as described herein is provided. The block of material is cut into a first component 1012 and a second component 1014. The polymer material comprises a stiff configuration as described herein.

At a step 1020, the first component 1012 and the second component 1014 are shaped into first lens component 1022 and second lens component 1024 of the AIOL. The components can be shaped in one or more of many ways such as turning on a lathe, cutting, ablation, and other known methods of shaping optical lenses. Alternatively or in combination, the components may be molded. One or more of the components 1022, 1024 comprises a feature 1026 shaped to receive the opposing component (the feature 1026 may comprise an annular groove, for example). A channel 1028 can be provided to allow fluidic communication with the chamber 1036 of the AIOL. Alternatively or in combination, the channel 1028 can be formed when the first and second components are bonded together.

At a step 1030, the first and second components 1022, 1024 are bonded together with an adhesive 1032 provided in the feature 1026. The first component 1022 and the second component 1024 define a chamber 1036.

The adhesive 1032 comprises a prepolymer of the polymer of the components 1012 and 1014. Although the components are shown provided from a single block, the polymer material can be provided with separate blocks of material having similar polymer composition.

A haptic 1038 can be affixed to the AIOL 1035, such that an internal chamber of the IOL is fluidically coupled to the chamber of the haptic. The haptic may comprise a material similar to the AIOL, or a different material. The haptic 1038 may have a thickness 1039. For example, the AIOL may comprise an acrylate as described herein and the haptic 1038 may comprise a soft silicon material. The haptic may comprise a soft material inserted into the AIOL when the AIOL comprises a stiff configuration, for example.

The AIOL in the stiff configuration comprises a dimension 1034 across, such as a diameter. The AIOL may comprise a thickness 1048 extending between an anterior most portion of the AIOL body and the posterior most portion of the AIOL body.

At a step 1040, the AIOL 1035 is hydrated to a substantially hydrated configuration to decrease stiffness, such that the AIOL comprises a soft material. In the hydrated configuration dimensions of the AIOL increase, and may increase proportionally to each other. In many embodiments, the increase comprises a similar percentage increase along each dimension.

In many embodiments, the amount of hydration in the stiff configuration comprises a predetermined amount of hydration in order to accurately machine the lens components to an appropriate amount of refractive power when the AIOL comprises the fully hydrated state when implanted in the eye.

The disc shaped optical structure of the upper component 1022 can be flat, or lens shaped, for example. The disc shaped optical structure of the lower component 1022 can be flat, or lens shaped, for example, such that one or more of the optical structures deforms to provide optical power.

Figure 11:
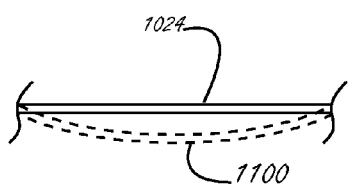
FIG. 11 shows an optical structure deformed to provide optical power.

FIG. 11 shows one or more of the optical structure deformed to provide optical power with a curved surface 1100. The fluid of the AIOL can be greater than the index of refraction of 1.33 of the aqueous humor in order to provide the increased optical power with curved surface 1100.

While reference is made to acrylates, the polymer and prepolymer may comprise silicone hydrogel materials, for example.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the inventions of the disclosure. It is intended that the following claims define the scope of invention and that methods and structures within the scope of these claims and their equivalents be covered thereby.

What is claimed is:

1. A method of manufacturing an accommodating intraocular lens, the method comprising:
providing a first lens component comprising a polymer, the first lens component comprising a first inner surface region extending discontinuously and circumferentially around a center of the first lens component and a first outer surface region extending circumferentially around the first inner surface region;
providing a second lens component comprising the polymer, the second lens component comprising a second inner surface region extending discontinuously and circumferentially around a center of the second lens component and a second outer surface region extending circumferentially around the second inner surface region;
bonding the first inner and outer surface regions of the first lens component to the second inner and outer surface regions of the second lens component with an adhesive comprising a prepolymer of the polymer, wherein the prepolymer is cured to bond the first lens component to the second lens component with the cured prepolymer extending between the first and second inner surface regions and between the first and second outer surface regions; thereby creating an inner seam and an outer seam, respectively, the inner seam defining an inner fluid chamber enclosed therewithin and the inner and outer seams defining an outer haptic chamber enclosed therebetween, the outer haptic chamber being in fluid communication with the inner fluid chamber; and
hydrating the bonded first lens component, the second lens component, and the cured prepolymer to provide a hydrated, soft accommodating intraocular lens comprising the polymer.

2. A method as in claim 1, wherein the first lens component and the second lens component each comprise a stiff configuration when the first lens component is bonded to the second lens component, with the cured prepolymer at the inner and outer seams extending between the first lens component and the second lens component.

3. A method as in claim 1, wherein hydrating the first lens component, the second lens component and the adhesive comprises fully hydrating the polymer of each of the components and the adhesive to an amount of hydration corresponding to an amount of hydration of the polymer when implanted.

4. A method as in claim 1, wherein each of the first lens component, the second lens component, and the cured adhesive each comprise a stiff configuration prior to hydration and a soft configuration when hydrated and wherein each of the first lens component, the second lens component, and the cured adhesive expand a substantially similar amount from the stiff configuration to the soft configuration in order to inhibit stress at interfaces between the adhesive and the first and second components.

5. A method as in claim 1, further comprising providing the polymer material and shaping the first lens component and the second lens component from the polymer material.

6. A method as in claim 5, wherein the first lens component and the second lens component are each turned on a lathe when stiff in order to shape the first lens component and the second lens component.

7. A method as in claim 5, wherein the first lens component and the second lens component are molded.

8. A method as in claim 1, wherein the prepolymer comprises one or more of a monomer, an oligomer, a partially cured monomer, particles, or nano particles of the polymer.

9. A method as in claim 1, wherein the first lens component comprises a first disc shaped structure, which includes the first inner surface region, and the second lens component comprises a second disc shaped structure, which includes the second inner surface region, and wherein the first component and the second component define the inner fluid chamber with the first and second disc shaped structures on opposite sides of the inner fluid chamber when bonded together.

10. A method as in claim 9, wherein one or more of the first lens component or the second lens component comprises an annular structure or an array of circumferentially distributed structures extending between the first disc structure and the second disc structure in order to separate the first disc structure from the second disc structure and define a side wall separating the inner fluid chamber from the outer haptic chamber.

11. A method as in claim 1, wherein one or more of the first inner surface region of the first lens component or the second inner surface region of the second lens component comprises a groove sized and shaped to receive the opposite inner surface, and wherein the adhesive is placed on the groove.

12. A method as in claim 1, wherein one or more of the first outer surface region of the first component or the second outer surface region of the second component comprises a groove sized and shaped to receive the opposite outer surface, and wherein the adhesive is placed on the groove.

13. A method as in claim 1, wherein both the first and second outer surface regions extend continuously circumferentially therearound to define the outer haptic chamber.

14. A method as in claim 1, further comprising filling one or more of the inner fluid chamber or outer haptic chamber with a fluid.

15. A method as in claim 14, wherein the fluid comprises one or more of a solution, an oil, a silicone oil, a solution of high molecular weight molecules, or high molecular weight dextran.

16. A method as in claim 14, wherein the fluid has an index of refraction greater than an index of refraction of an aqueous humor of an eye.

* * * * *